(12) United States Patent
Hancock et al.

(10) Patent No.: US 10,531,918 B2
(45) Date of Patent: Jan. 14, 2020

(54) ELECTROSURGICAL FORCEPS FOR DELIVERING MICROWAVE ENERGY FROM A NON-RESONANT UNBALANCED LOSSY TRANSMISSION LINE STRUCTURE

(71) Applicant: CREO MEDICAL LIMITED, Chepstow, Monmouthshire (GB)

(72) Inventors: Christopher Paul Hancock, Bath (GB); Malcolm White, Chepstow (GB)

(73) Assignee: CREO MEDICAL LIMITED, Chepstow (GB)

(*) Notice: Subject to any disclaimer, the term of this patent is extended or adjusted under 35 U.S.C. 154(b) by 0 days.

(21) Appl. No.: 16/444,980

(22) Filed: Jun. 18, 2019

(65) Prior Publication Data

US 2019/0298446 A1 Oct. 3, 2019

Related U.S. Application Data

(62) Division of application No. 15/021,936, filed as application No. PCT/GB2014/053015 on Oct. 7, 2014.

(30) Foreign Application Priority Data

Oct. 7, 2013 (GB) .................................. 1317713.4

(51) Int. Cl.
*A61B 18/18* (2006.01)
*A61B 18/00* (2006.01)

(52) U.S. Cl.
CPC .. *A61B 18/1815* (2013.01); *A61B 2018/0063* (2013.01); *A61B 2018/00404* (2013.01);
(Continued)

(58) Field of Classification Search
CPC .......... A61B 18/1815; A61B 18/00482; A61B 2018/0404; A61B 2018/00589;
(Continued)

(56) References Cited

U.S. PATENT DOCUMENTS 6,224,593 B1 5/2001 Ryan et al.
6,585,735 B1 7/2003 Frazier et al.
(Continued)

FOREIGN PATENT DOCUMENTS

EP 2 233 098 A1 9/2010
EP 2 412 328 A1 2/2012
(Continued)

OTHER PUBLICATIONS

International Search Report and Written Opinion of PCT/GB2014/053015 dated Dec. 12, 2014.
(Continued)

*Primary Examiner* — Ronald Hupczey, Jr.
*Assistant Examiner* — Rachel A. Vierra
(74) *Attorney, Agent, or Firm* — Arent Fox LLP

(57) ABSTRACT

Electrosurgical forceps for delivering microwave energy into biological tissue from a non-resonant unbalanced lossy transmission line structure located within or formed by the jaws of the forceps. The transmission line structure may be formed across the gap between the jaw element by opposed conductive elements, which are respectively electrically connected to inner and outer conductors of a coaxial cable. Alternatively, each jaw element may comprise its own lossy transmission line, whereby a power splitter is used to divide microwave energy from the coaxial cable. The forceps may be used endoscopically in the gastrointestinal tract or laparoscopically or in open surgery.

14 Claims, 5 Drawing Sheets

(52) U.S. Cl.
CPC ............. *A61B 2018/00482* (2013.01); *A61B 2018/00589* (2013.01); *A61B 2018/00595* (2013.01); *A61B 2018/1861* (2013.01)

(58) Field of Classification Search
CPC .. A61B 2018/00595; A61B 2018/0063; A61B 2018/1861
See application file for complete search history.

(56) References Cited

U.S. PATENT DOCUMENTS

| | | | |
|---|---|---|---|
| 9,050,115 | B2 | 6/2015 | Hancock |
| 9,236,646 | B2 | 1/2016 | Hancock |
| 2010/0137857 | A1 | 6/2010 | Shroff et al. |
| 2010/0249769 | A1* | 9/2010 | Nau, Jr. ............... A61B 18/18 606/33 |
| 2012/0143180 | A1 | 6/2012 | Lee, Jr. et al. |
| 2013/0144284 | A1 | 6/2013 | Behnke, II et al. |
| 2014/0194865 | A1 | 7/2014 | Tani et al. |

FOREIGN PATENT DOCUMENTS

| | | |
|---|---|---|
| EP | 2 556 794 A1 | 2/2013 |
| EP | 2 601 904 A1 | 6/2013 |
| GB | 2487288 A | 7/2012 |
| JP | 2010-505571 A | 2/2010 |
| JP | 2010-221037 A | 10/2010 |
| JP | 2010-227431 A | 10/2010 |
| JP | 2012-533378 A | 12/2012 |
| JP | WO 2013/022077 A1 | 2/2013 |
| WO | WO 03/020339 A2 | 3/2003 |
| WO | WO 2012/095654 A1 | 7/2012 |

OTHER PUBLICATIONS

British Search and Examination Report of related British Patent Application No. GB1417680.4 dated Mar. 17, 2015.
British Search Report of related British Patent Application No. GB1317713.4 dated Apr. 16, 2014.
Japanese Office Action of related Japanese Patent Application No. 2016-546185 dated Jul. 3, 2018.

* cited by examiner

ELECTROSURGICAL FORCEPS FOR DELIVERING MICROWAVE ENERGY FROM A NON-RESONANT UNBALANCED LOSSY TRANSMISSION LINE STRUCTURE

CROSS-REFERENCE TO RELATED APPLICATIONS

This application is a Divisional of U.S. application Ser. No. 15/021,936, filed Mar. 14, 2016, which is a National Stage entry of International Application No.: PCT/GB2014/053015, filed Oct. 7, 2014, which claims priority to United Kingdom Patent Application No. 1317713.4, filed Oct. 7, 2013. The disclosures of the priority applications are hereby incorporated in their entirety by reference.

FIELD OF THE INVENTION

The invention relates to electrosurgical forceps for grasping biological tissue and for delivering microwave frequency energy into the grasped tissue to coagulate or cauterise or seal the tissue. In particular, the forceps may be used to seal blood vessels. The forceps may be inserted down the instrument channel of an endoscope or a gastroscope, or may be used in laparoscopic surgery or open surgery.

BACKGROUND TO THE INVENTION

Forceps capable of delivering heat energy into grasped biological tissue are known. The heat energy may cauterise the grasped tissue and facilitate coagulation or vessel sealing.

U.S. Pat. No. 6,585,735 describes an endoscopic bipolar forceps in which the jaws of the forceps are arranged to conduct bipolar energy through the tissue held therebetween.

EP 2 233 098 describes microwave forceps for sealing tissue in which the sealing surfaces of the jaws include one or more microwave antennas for radiating microwave frequency energy into tissue grasped between the jaws of the forceps.

SUMMARY OF THE INVENTION

At its most general, the present invention provides electrosurgical forceps in which microwave energy is delivered into biological tissue from a non-resonant unbalanced lossy transmission line structure located within or formed by the jaws of the forceps. The forceps may be used endoscopically in the gastrointestinal tract or laparoscopically or in open surgery.

According to a first aspect of the invention, there is provided an electrosurgical forceps comprising: a pair of jaw elements pivotable relative to each other to open and close a gap therebetween; a first conductive element mounted in one of the pair of jaw elements adjacent to the gap; a second conductive element mounted in the other one of the pair of jaw elements adjacent to the gap opposite the first conductive element; a coaxial cable for conveying microwave energy; and a signal transition portion at a distal end of the coaxial cable, the signal transition portion being arranged to connect the first conductive element to an outer conductor of the coaxial cable and to connect the second conductive element to an inner conductor of the coaxial cable, wherein the first conductive element and the second conductive element form a non-uniform unbalanced lossy transmission line to support the microwave energy as a travelling wave, and wherein the first conductive element and the second conductive element are non-resonant for the microwave energy along the travelling wave.

Herein the term "non-resonant" may mean that the electrical length of the transmission line (along the microwave energy travelling wave) is set to inhibit multiple reflections of the travelling wave, i.e. to prevent or inhibit the creation of a radiating standing wave. In practice this may mean that the electrical length of the transmission line is substantially different from a multiple of a quarter wavelength of the microwave energy (an odd or even multiple needs to be avoided depending on whether the distal end of the transmission line is an open circuit or a short circuit). It is particularly desirable for the transmission line to be non-resonant when there is biological tissue in the gap, i.e. in contact with the jaw elements. Thus, the electrical length of the transmission line may be set to avoid a multiple of a quarter wavelength of the microwave energy when the transmission line is loaded by the biological tissue in this way. Preferably the distal end of the transmission line is an open circuit, as this may enable the device to operate with radiofrequency (RF) energy as well as microwave energy.

Forming a non-resonant transmission line may prevent the device from radiating. The microwave energy is therefore delivered into tissue through leakage from the transmission line structure. By setting the length of the transmission line with knowledge of the loss level into biological tissue at the frequency of the microwave energy, the electrosurgical forceps of the invention can be arrange to deliver substantially all of the power received at the proximal end of the transmission line in a single transit of the travelling wave along the transmission line.

In other words, the geometry of the transmission line is selected, e.g. on the basis of simulations or the like, such that it exhibits high loss in biological tissue at the frequency of the microwave energy. Similarly, the geometry of the transmission line may ensure that much less power is lost when there is no tissue in the gap, but air instead. For example, the device may exhibit about 1 dB return loss, i.e. 80% of power reflected back to the generator, compared to 20% when there is tissue there. Thus, four times as much power can be delivered when tissue is present in the gap. Biological tissue is lossy, i.e. it is a good absorber of microwave energy.

The magnitude of the electric field produced by the forceps of the invention may be considerably lower than that produced by conventional bipolar RF forceps. The microwave frequency electric field used in the invention damages tissue in a fundamentally different way from RF energy, i.e. by denaturing tissue rather than cell rupture. The potential for accidental localised extreme damage is therefore much smaller than with RF devices that may generate a plasma or arc and burn. Moreover, the peak voltage required to produce effective dielectric heating with microwave energy may be less than 50 V, which is a factor of 10 lower that required for bipolar RF devices and a factor of 100 less than that required for monopolar RF devices. In the latter, the path for the RF current to flow is through the body via a return plate placed on the surface of the patient's skin. This presents a risk to the patient in terms of the high voltage requirement and also lack of control due to the current always wanting to take the path of least resistance. It could also cause an explosion to occur within the body due to a build-up of gases being ignited due to a spark, arc, micro plasma or breakdown occurring because of the high voltage levels associated with monopolar RF energy, e.g. 4,500 V peak, or bipolar RF energy, e.g. 500 V peak or greater. The high voltages associated with bipolar or monopolar RF instruments present as risk of explosion. In comparison, voltages associated with microwave coagulation may be between 5 V and 70 V peak. The device is therefore safer for the patient when in use in the environment found inside the patient's body.

The magnitude of the field may be controlled e.g. by controlling the power delivered to the forceps based on the size of the gap. This control may be permit the magnitude of the electric field to be independent of the size of the vessel or the thickness of the tissue located in the gap. This may present an advantage over conventional bipolar RF forceps.

Herein, "microwave frequency" may be used broadly to indicate a frequency range of 400 MHz to 100 GHz, but preferably the range 1 GHz to 60 GHz, more preferably 2.45 GHz to 30 GHz or 5 GHz to 30 GHz. Specific frequencies that have been considered are: 915 MHz, 2.45 GHz, 3.3 GHz, 5.8 GHz, 10 GHz, 14.5 GHz and 24 GHz.

The electrosurgical forceps of the invention may be configured for insertion down an instrument channel of an endoscope, or may be arranged for use in laparoscopic surgery or in a NOTES procedure or in a general open procedure.

Herein, the term "non-uniform" transmission line is used to designate an arrangement in which the conductive elements on opposing surfaces of the jaws are not in a uniform spatial relationship with each other along the length of the pair of jaw elements. For example, the conductive elements may comprise a first conductive plate mounted in one of the pair of jaw elements and a second conductive plate mounted in the other one of the pair of jaw elements, wherein the signal transition portion is arranged to connect the first conductive plate to an outer conductor of the coaxial cable and to connect the second conductive plate to an inner conductor of the coaxial cable. The conductive plates may each include a flat surface at or aligned with the surface of one of the jaw elements facing into the gap. This configuration may ensure an optimal power density in the gap between the plates, to ensure that the energy is delivered into biological tissue present in the gap.

The transmission line may form a parallel transmission line or parallel plate transmission line when the opposing surfaces of the conductive plates are parallel. However, this is not essential. Over a wide range of angles between the jaws, e.g. ±20° or more, the power will travel up between the jaws. The jaws might not be parallel for a number of reasons, such as because they are pivoted at one end or because the tissue held between them is not of the uniform thickness.

Each conductive plate may have a flat elongate structure, e.g. having a width of 1 to 6 mm and a length of 3 to 12 mm. For endoscopic use, each plate may have a width of 1 to 3 mm and a length of 3 to 6 mm. Preferably, each plate has identical dimensions. The preferred dimensions may depend on the microwave frequency. Where 5.8 GHz energy is used, the plates may have a width of 2 mm and a length of 4 mm. The conductive plates may have curved distal ends. Removing sharp corners may reduce the risk of bowel wall perforation when operating in the GI tract, and may prevent unwanted concentrations of microwave energy. The conductive plates may have curved proximal ends, e.g. at the point at which they connect to the signal transition portion. The thickness of the plates may be 0.5 mm or less.

The signal transition portion may include a linking member that extends from a distal end of the coaxial cable, the linking member comprising an extension of the inner conductor of the coaxial cable surrounded by a dielectric cover, wherein a distal end of the extension of the inner conductor of the coaxial cable is connected to the second conductive plate. The linking member may have a length of 3 mm or more. The linking member itself may form a non-uniform transmission line.

The signal transition portion may include an outer connector that extends from the outer conductor of the coaxial cable and electrically connects the outer conductor of the coaxial cable to the first conductive plate. The proximal end of the outer connector may be curved to wrap around the outer conductor of the coaxial cable. The outer connector may taper (i.e. decrease in width) as it extends away from the outer conductor of the coaxial cable.

In another aspect of the invention, each jaw element may comprise its own lossy transmission line. In this arrangement, a power splitter may be used to divide the power between a pair of transmission lines, one on each jaw element. Thus, according to a second aspect of the invention, there is provided an electrosurgical forceps comprising: a pair of jaw elements pivotable relative to each other to open and close a gap therebetween; a first transmission line structure mounted in one of the pair of jaw elements adjacent to the gap; a second transmission line structure mounted in the other one of the pair of jaw elements adjacent to the gap opposite the first transmission line structure; a coaxial cable for conveying microwave frequency energy; and a power splitter at a distal end of the coaxial cable, the power splitter being arranged to divide the microwave frequency energy conveyed by the coaxial cable between the first transmission line structure and the second transmission line structure, wherein each of the first transmission line structure and the second transmission line structure consist of an unbalanced lossy transmission line to support the microwave energy as a travelling wave, and wherein each of the first transmission line structure and the second transmission line structure have an electrical length along the travelling wave that is non-resonant for the microwave energy.

Each of the first transmission line structure and the second transmission line structure is a parallel transmission line or a coaxial transmission line. The power splitter may comprise an arrangement of flexible microstrip transmission lines or coaxial transmission lines. For example, the signal transition may comprise any of a Wilkinson power divider, an arrangement of two quarter wavelength transformers, a 3 dB power splitter or the like. If a Wilkinson power divider is used to split the power available at the distal end of the coaxial cable into two equal parts, then the signal transition may comprise two semi-circular or straight sections that are each a quarter wavelength long at the frequency of operation, i.e. the overall length of the splitter is a half wavelength at the operating frequency. In this arrangement the impedance of the transmission lines that form the two semi-circular or straight sections is set as $$Z_W = \sqrt{2} Z_0,$$

where $Z_W$ is the impedance of the line that forms the Wilkinson power divider and $Z_0$ is the characteristic impedance of the of the coaxial cable. In a preferred embodiment, the impedance of the coaxial cable is set to be the same as the transmission line inside the jaws, which in turn is set to be the same as the biological tissue to be treated.

In an arrangement where two quarter wavelength transformers are used, a virtual impedance exists at the proximal end of each quarter wavelength arm that has a value which is twice the impedance of the characteristic impedance of the transmission line that feeds this point, i.e. the impedance 'seen' at the end of the transmission line is equal to half the value of the virtual impedance. This assumes that the two quarter wave transformer sections are the same impedance, the impedance of the transmission line inside each of the two jaws is the same, and that each jaw makes good contact with the biological tissue, which is homogeneous and has a value of impedance that is the same or close to that of the impedance of the transmission lines inside the two jaws.

A further arrangement could use a transmission line cable with a characteristic impedance of $Z_0$ feeding a Wilkinson power divider, whose lines have an impedance of $\sqrt{2}Z_0$, where each arm is connected to a quarter wavelength transformer, which impedance matches the characteristic impedance $Z_0$ to the Impedance of the transmission lines within the jaws, which is well matched to the impedance of the tissue $Z_t$.

The pair of jaw elements may be biased apart, e.g. using springs or the like. The springs may be made from plastic or other suitable material that does not interfere with the manner in which the microwave frequency energy is lost between the conductive plates. Alternatively, the jaw elements may also be wholly or partially made from memory metal, e.g. Nitinol wire, and be opened and closed based on the application of heat applied to the structure (wire). This heat may be generated using a DC power source (resistive heating), which may involve the use of additional feed lines, or generated when the microwave field is applied to the jaws. For the latter, it may be desirable to include, i.e. paint or deposit, a section of lossy material within the jaws or on the jaws such that some of the microwave field is absorbed by the lossy material to produce local heat, which causes the jaws to close (or open).

The forceps may be mounted in a cylindrical sheath, i.e. an enclosure for the coaxial cable and the pair of jaw elements. The sheath may be retractable to expose the pair of jaw elements. The sheath may act as a protective cover to facilitate insertion of the forceps through the instrument channel of an endoscope. The diameter of the cylindrical sheath may be less than 2.8 mm.

The forceps may include a jaw closing mechanism in mechanical communication with the pair of jaw elements. For example, the jaw closing mechanism may include a handle and pull trigger in communication with the pair of jaw elements via one or more pull wires. The pull wires may extend alongside the coaxial cable through the sheath if the forceps are inserted through an endoscope. In one embodiment, the jaw closing mechanism may include a pantograph arranged to ensure that the jaw elements close together in such a way that their surfaces meet simultaneously along their length.

The pair of jaw elements may be rotatable, e.g. by rotating the sheath.

BRIEF DESCRIPTION OF THE DRAWINGS

Embodiments of the invention are discussed below in detail with reference to the accompanying drawings, in which.

DETAILED DESCRIPTION; FURTHER OPTIONS AND PREFERENCES

Figure 1:
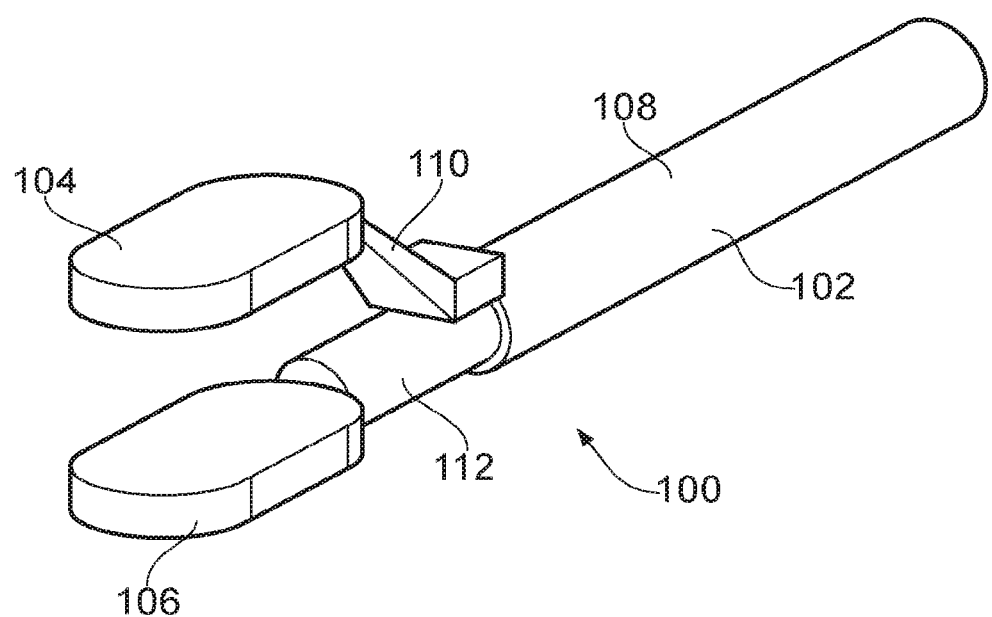
FIG. 1 is a modelled structure for an electrosurgical forceps that is an embodiment of the invention.

The present invention provides a microwave coagulating forceps that can be operated through the channel of an endoscope. The diameter of the channel in the endoscope may be 2.2 mm, 2.8 mm or 3.2 mm. The purpose of the forceps is to grasp a thin section of tissue and to coagulate or cauterise the portion held between the forceps using microwave energy, e.g. at a frequency of 5.8 GHz or more.

Unlike known microwave forceps, the present invention is not designed to radiate microwave energy. Instead, one or preferably both jaws of the forceps are designed to act as unbalanced lossy transmission lines. This function may arise from the selected geometry of the jaws.

An advantage of the lossy transmission line structure is that the delivery of power into tissue can be more accurately focussed in areas of contact with tissue. In known radiating devices, efficient antenna functionality may be based on contact between the whole antenna structure and the tissue, whereby the absence of tissue contact along the whole antenna length can prevent the antenna from operating efficiently which in turns affects the amount of energy that is delivered (and reflected back into the instrument). In this design, power will be delivered into the part that is held in the jaw elements, even if it only occupies (touches) part of the jaw elements. Most of the remaining power will be reflected back to the generator rather than being radiated out into the patient. This structure also offers clinical benefit in terms of the reflected microwave energy being reflected back along the jaws of the instrument may be utilised to produce enhanced tissue coagulation as it returns along a path back to the generator. At the distal end of the transmission line formed by the two jaws in contact with tissue, a total mismatch occurs due to the fact that the line is either in air or some other mismatched medium at this point, hence the reflection coefficient is unity or close to unity, i.e. all of the wave begins to travel back along the jaws back to the source). The transmission line structure works on the basis of reflection coefficient or impedance match, whereby if the impedance of the contact tissue is well matched to the impedance of the transmission line (reflection coefficient zero or close to zero). Ideally, all of the energy is absorbed by the biological tissue that makes contact with the jaws and so all of the energy is dissipated by the time it reaches the distal end of the jaws, hence no energy is reflected back along the transmission line structure within the jaws back to the generator. Since no resonance is required for the energy to be delivered, the electrical length of the transmission line on the jaw element is not constrained in the same way as it would be e.g. for an antenna. Accordingly, the electrical length of the transmission lines used in the present invention may be non-resonant at the frequency of the microwave energy (when the transmission line is loaded by biological tissue), i.e. not a multiple of a quarter loaded wavelength of the microwave energy.

The power delivered into the biological tissue at any point is given by:

$$P_t = P_i(1-\Gamma^2),$$

where $P_t$ is the power transmitted into the tissue at a particular point, $P_i$ is the incident power at the point where the transmission line makes contact with the tissue load, and $\Gamma$ is the reflection coefficient at that point, which is related to the impedance of the transmission line ($Z_0$) and the impedance of the tissue load ($Z_L$) by $$\Gamma = \frac{Z_L - Z_0}{Z_L + Z_0}.$$

The present invention may find particular use in the polypectomy procedures in the gastrointestinal (GI) tract, where the stem of a polyp needs to be sealed and cut. In such situations, the stem of the polyp may not contact all of the jaws of the forceps.

FIG. 1 shows a basic representative design for a microwave coagulating forceps that is an embodiment of the invention. The design is a model created using CST Microwave Studio®, which was then used to simulate the performance as various modifications were made to the structure to optimise the return loss and power density in biological tissue.

Although the examples below discuss the use of the forceps in an endoscope, the present invention need not be limited in this way. It may be applicable to laparoscopic techniques or used in open surgery.

FIG. 1 shows a pair of microwave coagulating forceps 100 that is an embodiment of the invention. The forceps 100 comprise a coaxial cable 102 for conveying microwave energy from a suitable generator (not shown) down an endoscope instrument channel to a pair of jaw elements 104, 106. The generator may be any device capable of delivering a controllable and stable microwave signal. For example, the apparatus disclosed in WO 2012/076844 may be used.

The coaxial cable 102 may be about 1.2 mm or 2.2 mm in diameter in order to allow room for a jaw operation mechanism in the instrument channel of the endoscope. Sucoform 47 manufactured by Huber+Suhner is a suitable cable that is 1.2 mm in diameter and is flexible enough to allow full manipulation of the endoscope with the cable within its channel.

In this embodiment, the jaw elements 104, 106 of the forceps are modelled as two conductive (e.g. metal) plates 0.5 mm thick and 2 mm wide with curved front and back ends. A first jaw element 104 is electrically connected to the outer conductor 108 of the coaxial cable 102 via an angled tapered connector 110. A second jaw element 106 is electrically connected to the inner conductor (not shown) of the coaxial cable by a linking member 112, which is an extension of the inner conductor and the dielectric 114 that surrounds it beyond the end of the outer conductor 108.

The jaw elements 104, 106 are movable relative to each other to open and close the gap between them. For example, the jaw elements 104, 106 may be connected to a hinge or pivot (not shown). The forceps 100 may thus include a jaw operation mechanism, which provided mechanical communication between the jaw elements and the distal end of the device. For example, the jaw operation mechanism may comprise one or more pull wires extending alongside the coaxial cable 102 through the instrument channel of the endoscope. Such jaw operation mechanisms are well known. In other embodiments, a pantograph arrangement may be used to open and close the jaw elements in such a way that their surfaces simultaneously meet all the way along their length.

The jaw elements 104, 106 may have a maximum separation of 2 mm, e.g. set by a stopper on the hinge. When pressed together, the jaw elements 104, 106 would present a distal cross-section area that measures 2.23 mm across the diagonal. This is small enough for an outer sheath (not shown) to fit around the jaw elements and still allow passage through the instrument channel of the endoscope. The sheath may act to protect the forceps (e.g. from damage or contamination) as it is inserted down the instrument channel of the endoscope, or to stop snagging or other damage as the tool is manipulated into position inside the patient. The sheath may be torque stable to assist rotation of the forceps. The sheath may be retractable to expose the jaw elements when the forceps are in position of use. Alternatively, the forceps may be extendable to protrude beyond the end of the sheath. In practice it is possible for the conductive plates that form the jaw elements to be thinner, e.g. 0.4 mm or less, as long as they retain sufficient stiffness to prevent unwanted flexing in use.

According to the invention, the function of the conductive plates is as unbalanced lossy transmission lines, whereby microwave frequency energy delivered to the jaw element leaks out into the surrounding environment. To optimise the geometry of the blades, the return loss of the modelled structure was simulated whilst varying a number of parameters, as shown in Table 1.

TABLE 1

Parameters varied simulations

| Run No. | Wire length (mm) | Plate length (mm) | Jaw width (mm) | Other |
|---|---|---|---|---|
| 0 | 9 | 5 | 2 | |
| 1 | 6 | 5 | 2 | |
| 2 | 4 | 5 | 2 | |
| 3 | 3 to 5 | 5 | 2 | |
| 4 | 4 | 3 to 6 | 2 | |
| 5 | 3 | 4 | 2 | |
| 6 | 3 | 4 | 2 | With balun |
| 7 | 3 | 4 | 0.75: to 3.25 | |
| 8 | 3 | 4 | 2 | |
| 9 | 3 | 4 | 2 | Gap 1 mm |

Figure 2:
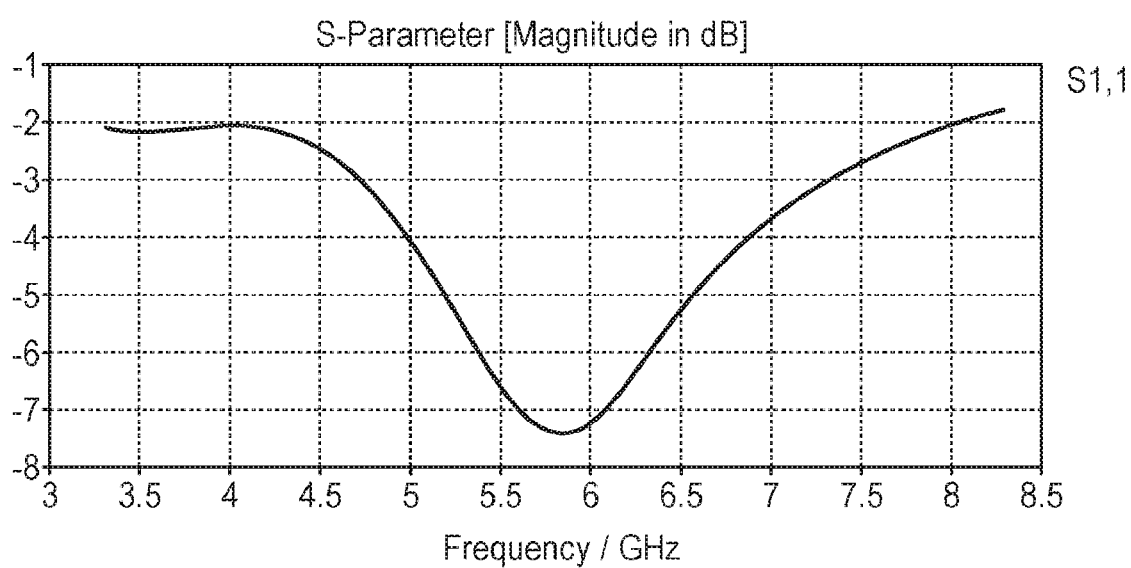
FIG. 2 is a graph showing return loss for a modelled example of an electrosurgical forceps that is an embodiment of the invention.

The parameter wire length corresponds to the length of the wire joining the coaxial cable to the conductive plates, e.g. the length of the connector 110 and linking member 112. In practice it is desirable for the wires to have a similar length. Any difference in length should be a small part, e.g. less than one eighth of a wavelength at the operating microwave frequency. It was found that with 3 mm wire length and 4 mm blade length the return loss was better than 7 dB at 5.8 GHz, as shown in FIG. 2. This means that less than 20% of the power is reflected back towards the generator, and over 80% is available for use at the conductive plates. This is reasonable efficiency, as any improvements could only increase the power available at the plates by less than 25%.

Figure 3:
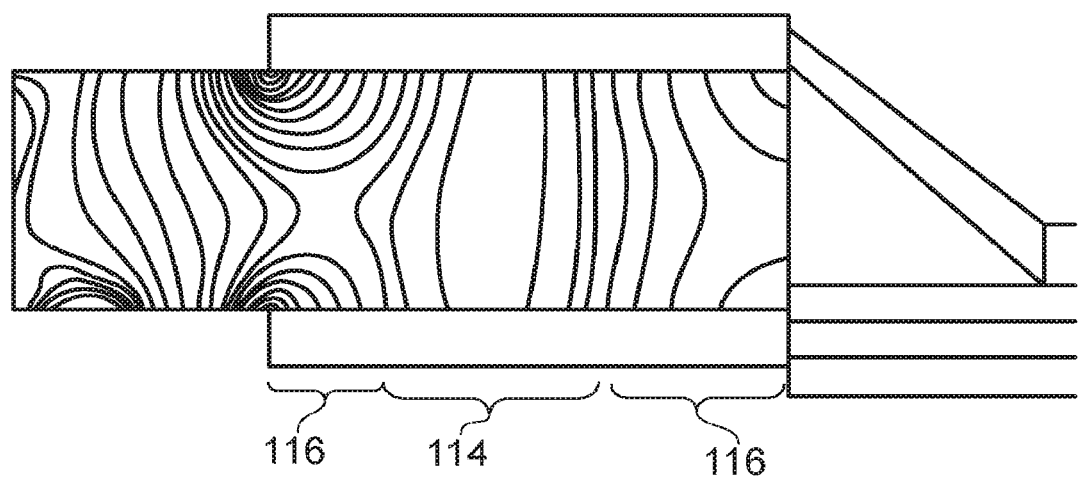
FIG. 3 is a side view of the modelled structure shown in FIG. 1 showing simulated power loss density in blood.

FIG. 3 shows the results of simulating power absorption in the region between the jaw elements for a 3 mm wire length and a 4 mm plate length when biological tissue (in this case blood) is present in that region. The power loss density differs between end regions 116 at the distal and proximal ends of the plates and a central region 114.

In the central region 114 the power loss density is about 65 dBW/m$^3$ for 1 W input power. In practice, it is expected that the device would be used with an input power of 10 W, whereby the power loss density (heating power) in this region would be 15 dBW/cm$^3$. This is about 30 W/cm$^3$ which is enough to raise the temperature of blood by about 7 Ks$^{-1}$, assuming that the specific heat capacity of tissue is about 4.2 J/g/K, and that the density of tissue is about 1 g/cm$^3$ so that the heat capacity of tissue is about 4.2 J/cm$^3$/K.

In the end regions 116, the heating rate will be about three times this, i.e. 20 Ks$^{-1}$.

In this example, the volume of the region between the plates is 4 mm long by 2 mm wide and 2 mm high, i.e. 16 mm$^3$. The average power density is about 90 W/cm$^3$, so the total power absorbed in this region is about 1.5 W. It is expected that blood or tissue that intrudes into the triangular gap where the connector 110 and linking member 112 flare out towards the plates would also be heated.

Figure 4:
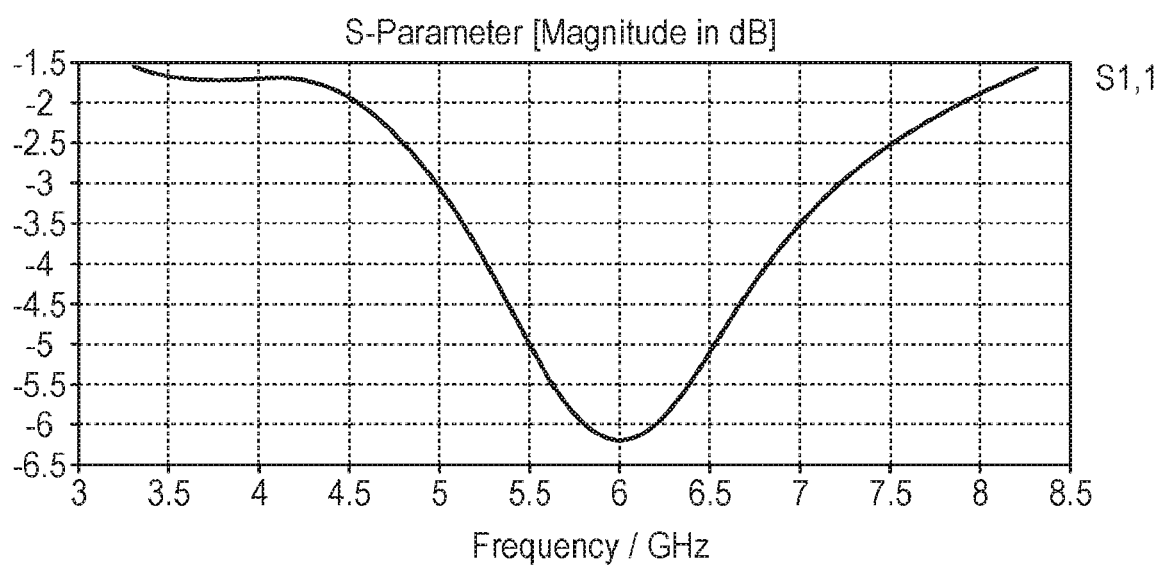
FIG. 4 is a graph showing return loss for another modelled example of an electrosurgical forceps that is an embodiment of the invention.

FIG. 4 shows the return loss when the separation of the plates is reduced to 1 mm. The return loss at 5.8 GHz changes from just more than 7 dB to just more than 6 dB. But despite this change, more than 75% of the incident power is available to heat the tissue.

Figure 5:
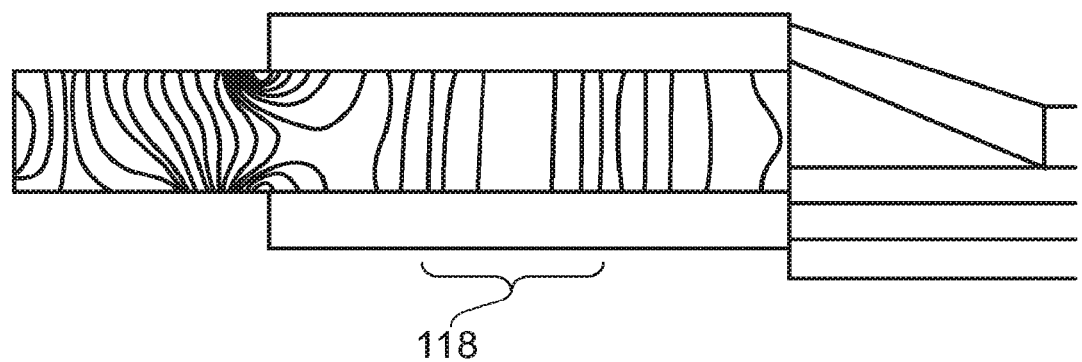
FIG. 5 is a side view of the modelled structure of FIG. 3 showing simulated power loss density in blood with a smaller spacing between jaw elements.

FIG. 5 shows the results of simulating power absorption in the region between the jaw elements for the smaller plate spacing, and it can be seen that the power loss density is higher, which might be expected because the slightly lower total power is concentrated in half the tissue thickness. The indicated power density in a central region 118 of the gap for 1 W incident power is about 66 dBW/m$^3$, which corresponds to about 38 W/cm$^3$ for 10 W incident power, which corresponds to a temperature rise of about 9 Ks$^{-1}$.

In a practical device, the jaw elements may be biased apart, e.g. using springs or the like. Such springs may be made from plastic, which will not affect the results of the simulations discussed above.

The shape of the connector 110 can be optimised to improve the transfer of microwave energy to the jaw elements 104, 106. In particular, it is desirable to hollow out the proximal end of the connector 110 at the coaxial cable 112 so that it curves around the dielectric 112. This geometry improves the return loss by making more gradual the change from the coaxial transmission line of the coaxial cable 112 to the twin transmission lines of the jaw elements 104, 106.

Figure 6:
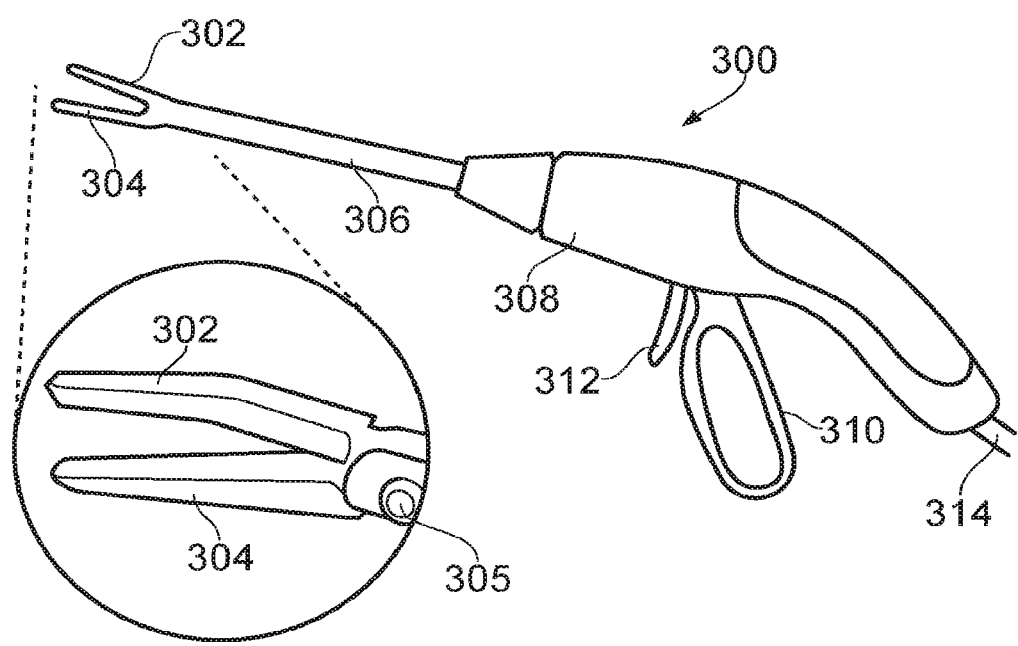
FIG. 6 is a schematic drawing of an electrosurgical forceps that is an embodiment of the invention.

FIG. 6 shows a schematic view of an endoscopic microwave forceps 300 that is an embodiment of the invention. The forceps 300 comprises a body 308 having a flexible feed cable 306 extending from it. The feed cable 306 is not drawn to scale; it has a length and diameter suitable for insertion down the instrument channel of an endoscope (not shown). This cable may be less than 2.8 mm in overall diameter to allow it to be inserted down the instrument channel of an endoscope or a gastroscope. The feed cable 306 comprises a outer sleeve that contains the coaxial cable and jaw opening mechanism discussed above. At a distal end of the cable 306 are a pair of jaw elements 302, 304, which are pivotable relative to each other about a hinge 305 to open and close a space between opposing surfaces thereof under the control of the jaw opening mechanism.

The body 308 includes a handle 310 and pull trigger 312 which operates the jaw closing mechanism in a conventional manner. The pull trigger 312 may alternatively be a mechanical slider or any other suitable mechanism that allow the jaws to be opened and closed. The body 308 is connected to a microwave signal generator (not shown) by a suitable cable 314.

The geometry of the jaw elements 302, 304 is selected so that they function as lossy transmission lines as discussed above.

Figure 7:
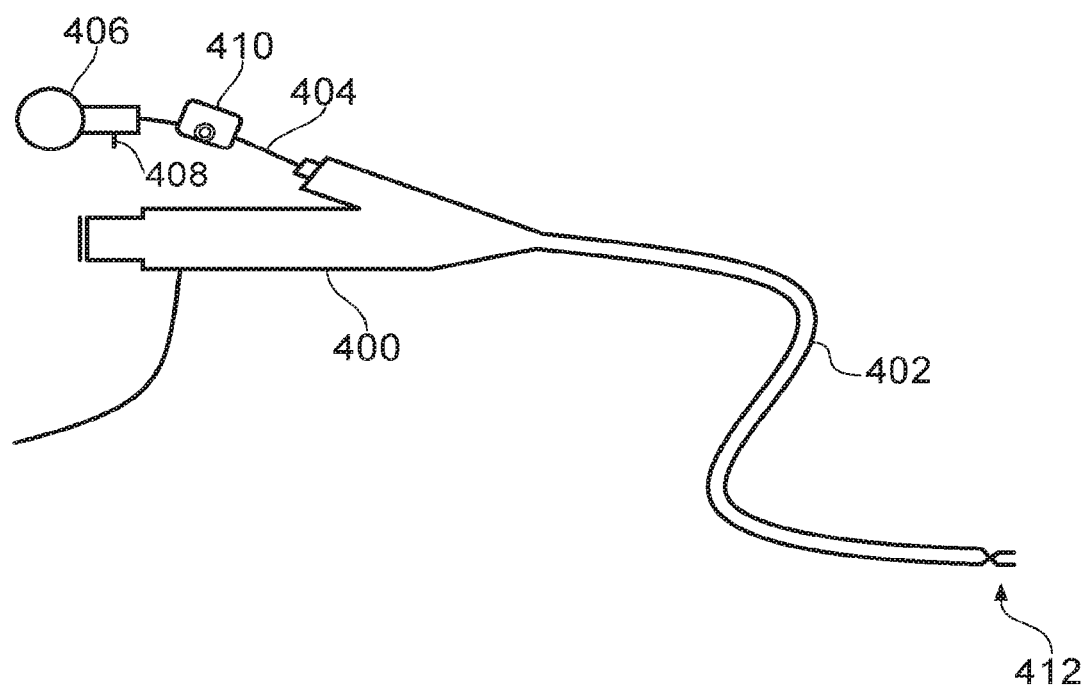
FIG. 7 is a schematic drawing of an endoscopic microwave forceps that is an embodiment of the invention.

FIG. 7 shows another embodiment of the invention, where the microwave forceps are inserted through the instrument channel 402 of an endoscope 400. The proximal end of the feed cable 404 terminates at a handle 406, which includes a pull trigger 408 for operating the jaw mechanism as discussed above. A hand grip 410 is clamped onto the feed cable to provide a means of rotating cable, and therefore controlling the orientation of the jaws 412 at the distal end of the cable. The outer sleeve of the feed cable may include internal braids which provide torque stability, i.e. resist twisting of the sleeve relative to the coaxial cable. Ideally, the translation between rotation of the handle at the proximal end of the device and the circular movement of the jaws at the distal end will be 1:1, but lesser translation ratios, e.g. 1:2 may be sufficient.

Figure 8A:
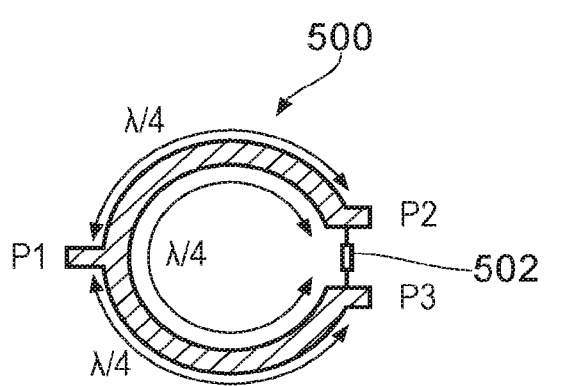
FIG. 8A shows a Wilkinson power divider arrangement that can be realised using flexible microstrip transmission line.

FIG. 8A shows a first configuration of a Wilkinson power divider 500, which functions to split an input power P1 into two equal parts (P2 and P3) using two quarter wavelength semi-circular lines or arms. Each arm may also function as an impedance transformer. Thus, the complete physical length of the structure is a half of the electrical wavelength at the frequency of operation. In order for this power splitting design to be used in practice, it may be preferable for the structure to be fabricated onto a flexible microwave substrate, where the tracks may be printed or photo etched. In order to balance the two output ports (P2 and P3), it is preferable to include a balancing resistor 502; the impedance value of this balancing resistor should preferably be twice the characteristic impedance.

Figure 8B:
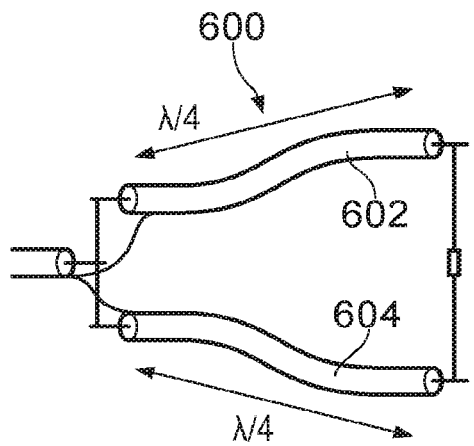
FIG. 8B shows a Wilkinson power divider arrangement that may be realised using coaxial transmission lines.

FIG. 8B gives a second configuration of a Wilkinson power divider 600. In this configuration, coaxial lines 602, 604 are used to realise the divider. If standard 75Ω coaxial cable is used for the quarter wavelength sections 602, 604, the divider will provide a reasonable match for 50Ω input and output ports. Ideally, if the input and output ports are 50Ω, then the impedance of each of the quarter wavelength arms is 70.71Ω (=√2×50). In practice, the coaxial impedance transformer should be as small and as flexible as possible in order to fit in the endoscope.

Figure 9A:
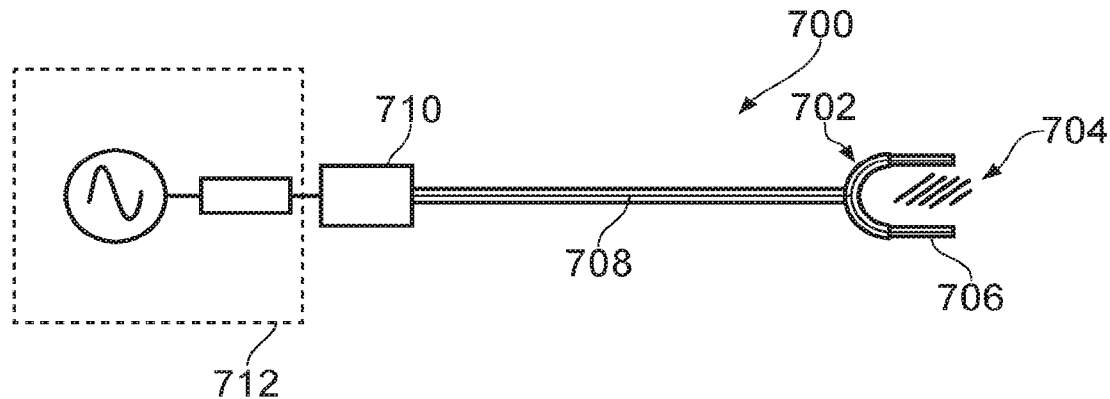
FIG. 9A shows a first design for electrosurgical forceps that uses a Wilkinson power divider realised using transmission lines.

FIG. 9A shows a schematic outline for a first example microwave forceps device 700 that uses a Wilkinson power divider 702, where the impedance $Z_t$ of the biological tissue 704 at the frequency of operation is the same as the impedance of the transmission line 706 within the jaws and is also the same as the impedance of the coaxial cable 708 that connects the microwave energy generator to the device. In FIG. 9A a quarter wave transformer 710 is used at the proximal end between the output of the generator 712 and the coaxial cable 708 to match the output impedance $Z_s$ of the generator 712 to the impedance of the coaxial cable 708 (which in this embodiment is also the impedance of the biological tissue 704 and the impedance of the transmission line 706 within the jaws). The impedance of the quarter wavelength transformer 710 is set as $\sqrt{Z_s \times Z_t}$. Normally, the output impedance of the microwave energy generator 712 will be 50Ω and if it is assumed that the impedance of blood is 25Ω at the preferred frequency of operation, then the impedance of the quarter wavelength transformer 710 will need to be 35.36Ω. This transformer could be realised in practice using a standard 50Ω co-axial transmission line with the diameter of the inner conductor increased, the inner diameter of the outer conductor reduced, the value of relative permittivity (dielectric constant) of the material that separates the inner and outer conductors increased, or by varying a combination of these parameters. It would be relatively straightforward to manufacture 25106 co-axial transmission line.

Figure 9B:
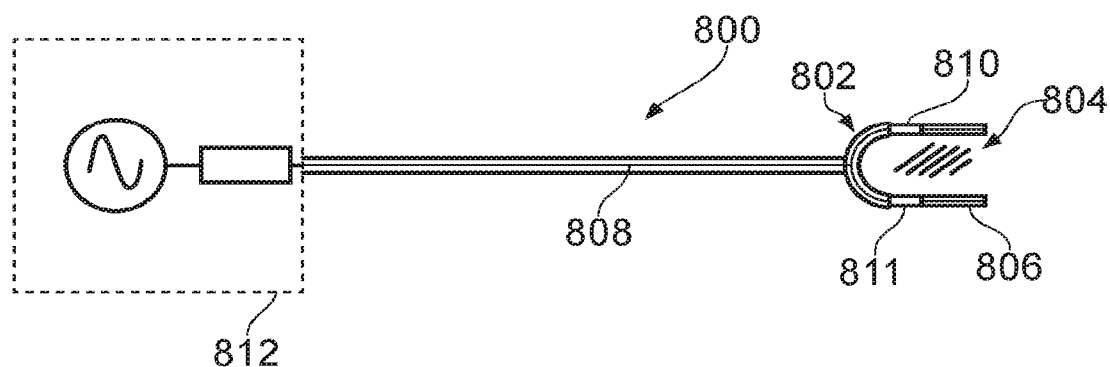
FIG. 9B shows a second design for electrosurgical forceps that uses a Wilkinson power divider realised using transmission lines.

FIG. 9B shows a schematic outline for a second example microwave forceps device 800 that uses a Wilkinson power divider 802, where the impedance $Z_0$ of the coaxial cable 808 that connects the generator 812 to the instrument is the same as the output impedance $Z_s$ of the generator, which is nominally 50Ω. In FIG. 9B there is a quarter wavelength transformer 810, 811 located between the distal end of each arm of the Wilkinson power divider 802 and the proximal end of a respective transmission line 806 that couples to the biological tissue 804. In this example, if it is assumed that the impedance $Z_t$ of the biological tissue is well matched to the impedance of the transmission lines 806 within the jaws, then the impedance of the quarter wavelength matching transformers 810 is $\sqrt{Z_0 \times Z_t}$.

Figure 9C:
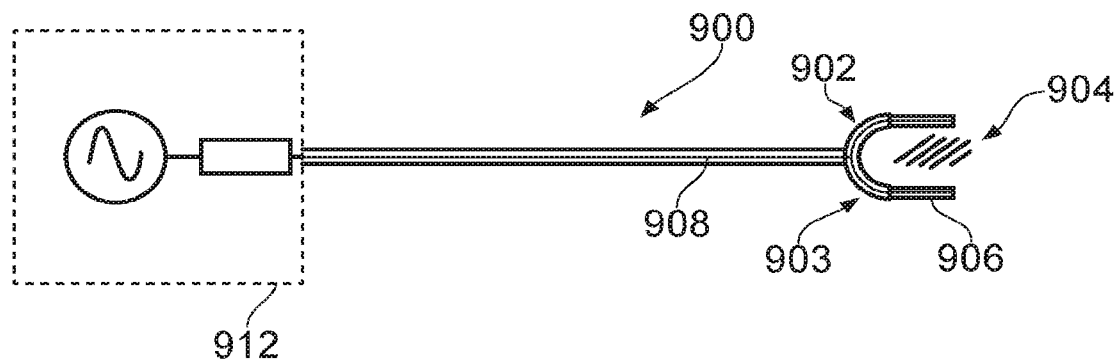
FIG. 9C shows a third design for electrosurgical forceps that uses a Wilkinson power divider realised using transmission lines.

FIG. 9C shows a schematic outline for a third example microwave forceps device 900 that uses a pair of quarter wavelength transmission line transformer sections 902, 903 to match the impedance of the biological tissue 904 to the impedance of the coaxial cable 908 and the microwave energy generator 912 to ensure efficient power transfer between the generator and the tissue load. Again, in this configuration it is assumed that the impedance of the transmission line 906 within the jaws is well matched to the impedance of the biological tissue $Z_t$. In this arrangement, each transformer 902, 903 transforms the impedance 'seen' at the jaws to a virtual impedance that has a value equal to twice the characteristic impedance of the coaxial cable 908, such that the proximal end of the two arms of the transformers are connected in parallel to give an impedance that is equal to the characteristic impedance of the feed cable (main microwave transmission line). The impedance $Z_0$ of the coaxial cable 908 may be the same as the output impedance $Z_s$ of the generator 912, and so the function of the two quarter wavelength impedance transformers is to match $Z_0$ to $Z_t$. It may also be noted that the two transformers are connected in parallel at this point, therefore, the impedance seen at the proximal end of each of the quarter wavelength impedance transformers is $2Z_0$. Thus, the impedance of the quarter wavelength matching sections 902, 903 is $\sqrt{2Z_0 \times Z_t}$.

The invention claimed is:

1. Electrosurgical forceps comprising:
a pair of jaw elements pivotable relative to each other to open and close a gap therebetween;
a first transmission line structure mounted in one of the pair of jaw elements adjacent to the gap;
a second transmission line structure mounted in the other one of the pair of jaw elements adjacent to the gap opposite the first transmission line structure;
a coaxial cable for conveying microwave frequency energy; and
a power splitter at a distal end of the coaxial cable, the power splitter being arranged to divide the microwave frequency energy conveyed by the coaxial cable between the first transmission line structure and the second transmission line structure,
wherein each of the first transmission line structure and the second transmission line structure consist of an unbalanced lossy transmission line to support the microwave energy as a travelling wave, and
wherein each of the first transmission line structure and the second transmission line structure have an electrical length along the travelling wave that is non-resonant for the microwave energy.

2. Electrosurgical forceps according to claim 1, wherein each of the first transmission line structure and the second transmission line structure is a parallel transmission line.

3. Electrosurgical forceps according to claim 1, wherein each of the first transmission line structure and the second transmission line structure is a coaxial transmission line.

4. Electrosurgical forceps according to claim 1, wherein the power splitter is a Wilkinson power divider.

5. Electrosurgical forceps according to claim 4, wherein the Wilkinson power splitter is fabricated using flexible microstrip transmission lines or coaxial transmission lines.

6. Electrosurgical forceps according to claim 1, wherein the power splitter comprises a pair of quarter wavelength transmission lines arranged to match a characteristic impedance of the coaxial cable to an impedance of the first transmission line structure and second transmission line structure.

7. Electrosurgical forceps according to claim 6, wherein the characteristic impedance of the coaxial cable is set to a predetermined impedance corresponding to a biological tissue to be treated, and an impedance of each quarter wavelength arm of the power splitter is equal to $\sqrt{2}$ times the predetermined impedance.

8. Electrosurgical forceps according to claim 1, including a quarter wavelength impedance transformer at a proximal end of the coaxial cable, the quarter wavelength impedance transformer being arranged to match an impedance of the coaxial cable to a generator for delivering the microwave frequency energy into the coaxial cable.

9. Electrosurgical forceps according to claim 1, wherein the pair of jaw elements are biased apart.

10. Electrosurgical forceps according to claim 1, including a sheath for enclosing the coaxial cable and the pair of jaw elements, wherein the sheath is retractable to expose the pair of jaw elements.

11. Electrosurgical forceps according to claim 10, wherein the sheath is cylindrical and has a diameter less than 2.8 mm.

12. Electrosurgical forceps according to claim 10, including a handle clamped around a proximal end of the sheath for transmitting rotational motion to the sheath.

13. Electrosurgical forceps according to claim 1, including a jaw closing mechanism in mechanical communication with the pair of jaw elements.

14. Electrosurgical forceps according to claim 13, wherein the jaw closing mechanism includes a pantograph arranged to ensure that the pair of jaw elements close together in such a way that their surfaces meet simultaneously along their length.

* * * * *